United States Patent [19]

Linder

[11] 4,281,545

[45] Aug. 4, 1981

[54] ASPIRATOR FOR AIR SAMPLING

[76] Inventor: Ernst C. G. Linder, Linnegatan 102, S-11523 Stockholm, Sweden

[21] Appl. No.: 177,751

[22] PCT Filed: Apr. 24, 1979

[86] PCT No.: PCT/SE79/00099

§ 371 Date: Dec. 24, 1979

§ 102(e) Date: Dec. 21, 1979

[87] PCT Pub. No.: WO79/00981

PCT Pub. Date: Nov. 29, 1979

[30] Foreign Application Priority Data

Apr. 24, 1978 [SE] Sweden .............................. 7804649

[51] Int. Cl.³ .............................................. G01N 1/24
[52] U.S. Cl. .................................................. 73/864.62
[58] Field of Search ............... 73/421.5 R, 425, 425.6, 73/23; 422/100

[56] References Cited

U.S. PATENT DOCUMENTS

| 3,884,081 | 5/1975 | Griffith | 73/421.5 R |
| 3,933,029 | 1/1976 | Rabenecker et al. | 73/23 |
| 4,080,832 | 3/1978 | Moody et al. | 73/421.5 R |

FOREIGN PATENT DOCUMENTS 865404  3/1971  Canada .................................. 73/425.6

Primary Examiner—James J. Gill
Attorney, Agent, or Firm—Finnegan, Henderson, Farabow, Garrett & Dunner

[57] ABSTRACT

An aspirator for air sampling, the air samples being sucked into a glass vessel for a certain period of time. The aspirator can be carried in a pocket, for example, by the one whose working environment is being analyzed. In a casing there is disposed a replaceable cylinder (2) with associated plunger (4). The plunger is intended to be pulled in by a motor unit (12) and gearbox, arranged adjacent the cylinder (2), the unit (12) rotating a drum (8) onto which is wound a string. The other string end is fixed, via a pulley (7), to the spring-loaded plunger (4). When air has been sucked in to a sufficient amount, the opening (3) of the cylinder is closed and the plunger can be released from the string and the spring, which is possible since the plunger is only magnetically retained (4).

3 Claims, 1 Drawing Figure

U.S. Patent   Aug. 4, 1981   4,281,545
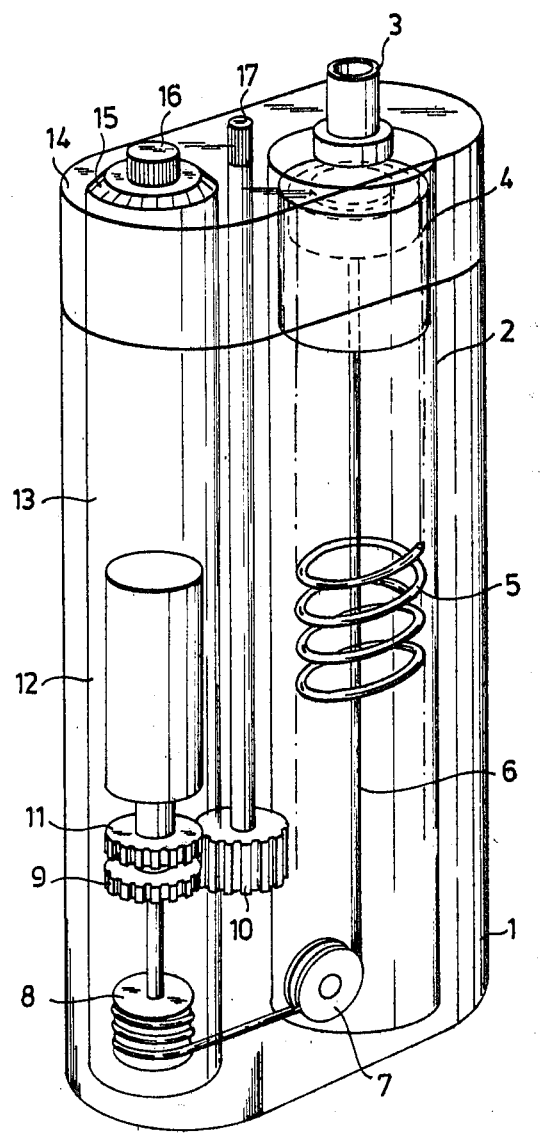

ASPIRATOR FOR AIR SAMPLING

The ever increasing emphasis on worker protection has directed more and more attention to the necessity of obtaining objective evaluations of the working environment. One of the most important factors in this respect is the quality of the air in which the employees work. For this reason, special sampling devices have come on the market, designed to take samples, on site, of the air and bring these samples to a laboratory for analysis. The techniques of gas chromatography have come to be quite important for this sampling.

In sampling of this type, there are, in principle, two different, rather separate methods. In one of them the sampler is a pump which forces the air at a certain speed through a special filter, usually of the activated carbon type. The contents of the filter are then analyzed in the laboratory. Although such a device is of great value for checking, for example, for the presence and levels of vapors of certain solvents in paint-spraying shops, for example, it is in many cases desirable to obtain samples which are representative of pollutants with less adhesion to a filter of the type mentioned. Furthermore, the problem arises, when attempting to evaluate the test results exactly, that the ability of the filter to absorb gaseous pollutants is different for different substances, different sampling temperatures etc.

Therefore, there is an alternative technique which takes complete samples of the air, that is to say, the sample taken is, quite simply, a representative quantity of air. A known device for taking such samples consists of a bracket with an electric motor, on which bracket a conventional injection glass syringe is mounted whose plunger, which is also made of glass, is disposed to be moved at fairly constant speed by means of the motor. This device is carried on the back of a person active in the working environment in question, and a hose is coupled between the intake hole of the cylinder and an intake nozzle which is normally attached to the chest to obtain a sample which is representative for the air which the person is to breath. A great disadvantage with this device is its weight, which in current models is about 1.5 kg, as well as the uncomfortable back mounting.

It is a purpose of the present invention to achieve an aspirator for complete air sampling, which is so light that it can be comfortably carried by a person in a breast-pocket or the like, for example. Another purpose is to achieve a device of this type which makes possible simple replacement of an air ampule containing a collected air sample with a new ampule for further sampling. Other purposes and advantages are evident from the description below.

These purposes and advantages are achieved according to the invention by an aspirator for taking air samples, which has the characteristics disclosed in claim 1.

The invention will now be described in more detail based on an example in connection to the drawing which shows an aspirator for air sampling designed to be placed in a breast-pocket, for example.

The FIGURE shows an X-ray picture of an aspirator, disposed in a casing 1 with a cover 14. It can, as will be discussed below, be advantageous to make the casing of transparent material, acrylic plastic for example, but opaque material can also be used for the casing.

In the casing there is mounted a pump cylinder 2 with a plunger 4. The upper end of the pump cylinder is provided with an intake opening which can be sealed, either by a stopcock (not shown) or quite simply by a removable plug. The intention is to move the plunger downwards at an even speed through the mechanical means described below, whereby the surrounding air is sucked in for subsequent analysis in the laboratory.

The pump cylinder is suitably made of glass with a ground-in plunger approximately of the type used in hypodermic syringes modified in the manner which will be described here. After an air sample has been taken, it can be desirable to take out the pump cylinder with its plunger. This is done most simply by closing the opening at 3, lifting off the cover 4 and taking out the pump cylinder with the piston inside, which is sufficiently short, even with an air sample in the cylinder, to be housed completely within the cylinder. By virtue of the fact that the opening at 3 is closed and the fact that the fit of the plunger is good, the entire unit can be removed without air being drawn in or released. The pump cylinder with plunger is then suitably placed in a storage box, possibly intended for a number of samples, and which during transport supports the plunger, for example at a point corresponding to the position of the piston when an air sample has been taken.

In the casing there is also a mechanism for pulling out the plunger in the cylinder at an even rate. This mechanism consists of an electric motor (or a watch movement) with a battery, and a suitable gearbox coupled to the motor. A drum is coupled after the gearbox and it is rotated by the outgoing shaft of the gearbox to wind up a string on it. The end of the string running from the drum continues via a block 7 and is coupled to the plunger to move the same. This is done under the countereffect of a spring 5 mounted under the plunger.

In the embodiment shown in the FIGURE, between the unit 12 which houses a motor and a gearbox and which is arranged together with a battery (not shown) and a switch 15 with a knob 16, in a cylinder (13) which is parallel to the pump cylinder and is removable when the cover 14 is taken off, there is arranged a coupling device consisting of a gear 9 connected to the drum, an intermediate gear 10 engaging therewith and a gear coupled to the motor unit 12 and engaging the intermediate gear. When the motor unit is withdrawn, the gear 11 is pulled out at the same time. As can be appreciated from the FIGURE, the drum can then be rotated by turning the protruding shaft 17, which is coupled to the intermediate gear 10. When removing the pump cylinder, the cylinder 13 need not be pulled out completely, since, after the cover and the cylinder have been lifted somewhat, the cover can be swung 180°.

The string is coupled to the plunger 4 in the following manner. The spring 5, fixed to the lower portion of the pump cylinder (in a manner not shown), has fixed to its upper portion a holder for a magnet. A ferromagnetic piece of metal is fixed inside the plunger 4 which is made of glass. During use, this magnetic piece of metal will be held fast by the magnet. The free end of the string is fastened to the magnet holder so that the plunger is drawn downwards when the string is rolled onto the drum 8. (It is, of course, possible to affix the magnet to the plunger if desired).

The advantage of the magnetic coupling between the plunger 4 and the string and the spring is that it is so practical when changing the pump cylinder and plunger. If the intake opening 3 is sealed, one can simply pull out the pump cylinder together with its plunger. It is true that the short-duration tractive force exerted on the plunger will cause the collected gas to expand somewhat, but this occurs elastically and the plunger returns to its original position as soon as the magnetic force has been overcome. By virtue of the fact that the plunger is ground to a good fit in the pump cylinder, no gas will be sucked in, thus leaving the sample unchanged.

In the example shown in the FIGURE, a plunger and pump cylinder taken from a glass hypodermic needle were used, in which the plunger was cut off to an appropriate length. As a motor unit, a motor of the type 15 C 11-113 was used and a gear box of type FM 15, made by Escap (from Portescap, La Chaux-de-Fonds, Switzerland). The gear box has a gear ratio of 128,000:1. By using an appropriate battery and series resistance (selectable by the switch 15) one can achieve induction of the full sample volume (30 ml) in 15 min., 30 min., 1 hour, 2 hours, 4 hours or 8 hours. With the selected motor and a rechargable battery (1.5 V), a fairly even induction can be obtained. The longest period with such a battery can present difficulties if the battery cannot be kept at room temperature, but which is normally the case, especially if the aspirator is kept in the pocket. If longer sampling times are desired, another motor arrangement and a stronger battery can be considered. They would, however, fit into the same casing. More complicated electronic motor-control means can also be used, of course.

One advantage of making the casing transparent is that one can follow the function and see the position of the plunger in the pump cylinder. It might also be advantageous to make the magnet holder in some very-noticable color.

It is advisable, if rechargable batteries are used, to make recharging possible on location by arranging a jack for connecting a wire to a charging unit.

It is advantageous that the collection of air samples be able to be done in glass containers, since this is an inert material with very little tendency to adsorb components from the sample. This is especially so since just those molecules which are especially interesting with regard to the working environment can have an especially great susceptability to such adsorption. It can also be possible to achieve an additional improvement in this respect if the glass is treated with polytetrafluoroethylene, which in thin layers tends to reduce this effect for certain substances. Such techniques have been developed at NBS and NPL, for example, to reduce the wall effect in glass containers used for the construction of hydrogen masers, which were developed to create a new definition of time.

As has already been mentioned, the above aspirator for air testing provides very significant advantages, not the least of which is the reduction in weight and size in comparison to the prior art. The weight of the example described, for instance, is merely about 300 grams as compared to the previous 1.5 kg.

A range of design alternatives will present itself to the person skilled in the art upon reading this description. It is intended that such design variations will be encompassed by the following patent claims.

I claim:

1. Aspirator for air sampling, there being arranged in a casing a removable pump cylinder (2) with accompanying plunger (4) and a motor (12) arranged to move the plunger for drawing in sample air through a sealable opening (3) in the pump cylinder, characterized in that the motor with an accompanying gearing device is arranged in the casing beside the pump cylinder and is coupled to a drum (8) arranged for winding up a string, the free end of the string being coupled to the plunger, which is biased by means of a spring (5) disposed in the casing, oppositely to the pulling direction of the string.

2. Aspirator according to claim 1, characterized in that the pump cylinder and the plunger are of glass and the plunger is so short in relation to the length of the pump cylinder, that the plunger at full extension for collecting a sample is still completely inside the pump cylinder.

3. Aspirator according to claim 1 or 2, characterized in that a holder with a magnet is mounted at the end of the spring (5) facing the plunger, said magnet being disposed to exert a pulling force on a magnetic piece of metal arranged on the outwardly facing portion of the plunger, the string being fastened to the holder fixed to the just-mentioned end of the spring, whereby the string and the spring are detachably coupled to the plunger.

* * * * *